United States Patent [19]

Kairy et al.

[11] Patent Number: 5,073,360
[45] Date of Patent: Dec. 17, 1991

[54] BRIDGE/LAMELLAR METALLIC OXIDES

[75] Inventors: Mostafa Kairy; Daniel Tinet, both of Orleans; Henri Van Damme, Olivet, all of France

[73] Assignee: Rhone-Poulenc Chimie, Courbevoie, France

[21] Appl. No.: 366,180

[22] Filed: Jun. 12, 1989

[30] Foreign Application Priority Data

Jun. 10, 1988 [FR] France ................................ 88 07748

[51] Int. Cl.$^5$ ................................................ C01F 1/00
[52] U.S. Cl. ...................................................... 423/608
[58] Field of Search ......................................... 423/608

[56] References Cited

U.S. PATENT DOCUMENTS

| 3,056,647 | 10/1962 | Amplett | 423/608 |
| 4,389,385 | 6/1983 | Ramsay | 423/608 |
| 4,724,135 | 2/1988 | Cirjak | 423/608 |
| 4,731,234 | 3/1988 | Wada | 423/608 |

FOREIGN PATENT DOCUMENTS

WO88/00093 1/1988 European Pat. Off.

OTHER PUBLICATIONS

Mario L. Occelli, Catalytic Cracking with an Interlayered Clay, A Two-Dimensional Molecular Sieve, 1983, vol. 22, No. 4, pp. 553–558.

Pierre Aldebert et al., $V_2O_5$ Gels: A Versatile Host Structure for Intercalation, May 1982, pp. 484–495.

*Primary Examiner*—Peter D. Rosenberg
*Attorney, Agent, or Firm*—Burns, Doane, Swecker & Mathis

[57] ABSTRACT

Bridged/lamellar metallic oxides, e.g., those of vanadium, molybdenum, tungsten and titanium, which have large and stable specific surfaces and are well adopted as catalysts, are prepared by (a) intimately admixing a gel of a metallic oxide having a lamellar structure with a cationic solution, (b) adding a solution of a spheroidal cationic species, e.g., a polyoxocation of aluminum, chromium, zirconium, nickel, molybdenum, niobium or tantalum, to the reaction medium thus produced, and then (c) aging the reaction medium for such period of time as to exchange the spheroidal cationic species for the cations introduced in step (a).

23 Claims, No Drawings

BRIDGE/LAMELLAR METALLIC OXIDES

BACKGROUND OF THE INVENTION

1. Field of the Invention

The present invention relates to the preparation of metallic oxides having a bridged lamellar structure and to the metallic oxides thus produced.

This invention more especially relates to the bridging of metallic oxides having a lamellar structure to produce metallic oxides having a high specific surface.

2. Description of the Prior Art

Considerable research has to date been carried out to prepare materials having a high specific surface which are particularly useful in adsorption, absorption or catalysis. The zeolites are the materials currently most typically used for these applications. Nonetheless, this art is actively seeking substitutes for the zeolites. Indeed, the zeolites have certain disadvantages, in particular the limitation on the size of the channels extending therethrough.

Among such possible substitutes, compounds having a bridged lamellar structure are considered especially interesting. Thus, numerous bridged clays comprising a variety of bridging structures are already known to this art.

By "bridging" is intended the insertion of ionic or nonionic chemical species between the lamella of the lamellar structure of a product, causing a swelling of the product by the spreading apart of the different planes, followed by the physical or chemical joining of said species with the lamella of the lamellar structure.

In the case in which the species inserted are not bonded, the phenomenon is reversible and is designated intercalation.

The intercalation and bridging of different metallic oxides having a lamellar structure are also known to this art. Thus, vanadium pentoxide gels have a lamellar structure and are characterized by colloidal particles in the form of strips which are capable of being stacked upon each other and which serve as the host for numerous chemical compounds, such as organic solvents, long chain cations or metallocenes, as described in the article of J. Livage et al.

The number of species that may be inserted, and in particular the cations, depend on the charge and the numerous sites present on each lamella or plane of the lamellar structure. In the case of clays, the charge is due to substitution of cations of silicon and/or aluminum for cations having a lesser charge. In vanadium pentoxide gels, the charge may be obtained by the reduction of vanadium cations. The intercalation then involves a transfer of electrons, combined with the insertion of the species to be intercalated into the lattice. However, this insertion may modify the structure or destroy the lattice, commencing at a certain degree of reduction.

To date it has not been possible to insert highly charged, large ionic species, such as of $[Al_{13}O_4(OH)_{24}]^{7+}$ type, into metallic oxides of vanadium pentoxide type, to effect particularly desirable catalytic properties.

SUMMARY OF THE INVENTION

Accordingly, a major object of the present invention is the provision of an improved process for inserting highly charged spheroidal ionic species into metallic oxides having a lamellar structure, without modifying or destroying the basic structure of the oxide. The final product metallic oxides, which have a bridged lamellar structure, conspicuously avoid, or at least ameliorate, those disadvantages and drawbacks to date characterizing the state of this art.

Briefly, the present invention features the preparation of metallic oxides having a bridged lamellar structure, comprising (a) mixing a gel of a metallic oxide having a lamellar structure, with a solution of inorganic cations having an e/r ratio higher than 2, wherein e is the electronic charge of the cation and r its ionic radius, in Angstroms, and/or of organic cations having a molecular diameter larger than 6 Å, (b) next adding to the reaction medium a solution containing a spheroidal ionic species, and (c) permitting said reaction mixture to stand for such period of time that an exchange takes place between the aforesaid cations and the spheroidal ionic species. Finally, the bridged metallic oxide is recovered by any known technique, for example by filtering and drying.

DETAILED DESCRIPTION OF THE PREFERRED EMBODIMENTS OF THE INVENTION

More particularly according to the present invention, the starting material gels of the lamellar metallic oxide advantageously comprise gels of vanadium pentoxide, molybdenum oxide and tungsten or titanium oxide.

By "spheroidal ionic species" are intended the complex cations having a large ionic radius, such as, for example, the polyoxocations of the metals aluminum, zirconium, chromium, molybdenum, niobium or tantalum, such as $[Al_{13}O_4(OH)_{24}]^{7+}$; $[Zr_4(OH)_{14}(H_2O)_{10}]^{4+}$; 8 $Mo_6Cl_{14}]^{4+}$; $[Nb_6Cl_{12}]^{2+}$; $[Ta_6Cl_{12}]^{2+}$.

The preferred spheroidal ionic species of the invention is the polyoxocation of aluminum and, in particular, the polyoxocation $[Al_{13}O_4(OH)_{24}]^{7+}$.

The inorganic cations having an e/r ratio higher than 2 suitable for use according to the invention are, in particular, those comprising the cations of the alkaline earths, cobalt, iron, manganese, copper, strontium, lithium, vanadyl oxide ($VO^{2+}$), aluminum, nickel, the lanthanides and, more particularly, of lanthanum.

Exemplary organic cations having a molecular diameter larger than 6 Å and also suitable for use according to the invention are the quaternary ammonium cations or quaternary phosphonium cations comprising substituted or unsubstituted aliphatic organic radicals containing from 3 to 20 carbon atoms.

Advantageously, if the metallic oxide is vanadium oxide ($V_2O_5$), the preferred cation is the $VO^{2+}$ cation. This cation is intercalated into the lamellar structure by exchange with one of its salts, for example the sulfate, $VOSO_4$.

In a preferred embodiment of the invention, the solution of the spheroidal ionic species has a pH lower than approximately 5, if the metallic oxide is vanadium oxide ($V_2O_5$).

Indeed, the vanadium oxide gel is not stable at higher pH values.

Preferably, the pH of the spheroidal ionic species ranges from approximately 3 to 4.5.

The molar ratio $OH^-/Al$ in the solution of the spheroidal ionic species ranges from 0 to 2.5, preferably from 1.2 to 2.2.

The solutions of the cations or spheroidal ionic species are generally aqueous solutions, but it is possible to use other solvents, such as, for example, methanol or ethanol.

The metallic oxide gels are prepared by conventional techniques, such as, for example, by precipitation of a precursor of such metallic oxide.

The preferred metallic oxide of the invention is vanadium pentoxide, in the form of a gel, having a concentration in $V_2O_5$ ranging from about 0.1% to 1% by weight of the metallic oxide.

As the spheroidal ionic species, the aluminum polyoxocation is the preferred. It may be represented by the formula $[Al_{13}O_4(OH)_{24}]^{7+}$. This spheroidal ionic species is added in a manner such that the reaction medium containing the $V_2O_5$ gel will contain an amount of aluminum ranging from approximately 13 mmole to 50 mmole per gram of $V_2O_5$. The concentration is expressed in moles of Al.

The mixture of the gel of the metallic oxide and the solution of the spheroidal is permitted to age, preferably for approximately 1 hour to 100 hours. However, the duration of aging is a function of temperature. Typically, the solution is aged at a temperature of from ambient to about 70° C.

After aging, the metallic oxide is separated from the reaction medium, for example by filtration.

The solids recovered in this manner are dried in air and optionally calcined prior to its use as an adsorbent or catalyst.

In a preferred embodiment of the invention, the filtered solids are first washed, in particular to eliminate the cations, such as the $VO^{2+}$ cations, inserted in the first stage of the process.

The washing may be carried out in conventional manner, with water. However, in a preferred embodiment of the invention, the washing is by dialysis.

This invention also features a vanadium oxide, per se, having a bridged lamellar structure, and wherein the distance between each plane, or the height of the interlamellar spacing, ranges from about 8 Å to 13 Å.

This vanadium oxide has a specific surface, as measured by the B.E.T. method, of greater than 20 m²/g. In a preferred embodiment of the invention, the specific surface ranges from approximately 50 to approximately 100 m²/g.

The vanadium oxide of the invention has a stable specific surface within the values indicated above, over a wide temperature range, in particular up to approximately 350° C.

In another preferred embodiment of the invention, the vanadium oxide contains, expressed by weight of aluminum, approximately 15% to 35% by weight aluminum polyoxocation, preferably from 25% to 35% by weight.

The compounds of the invention may be used as molecular sieve filters, or as catalysts or catalyst supports.

In order to further illustrate the present invention and the advantages thereof, the following specific examples are given, it being understood that same are intended only as illustrative and in nowise limitative.

EXAMPLES 1 TO 6

Preparation of a Vanadium Pentoxide Gel

A vanadium pentoxide gel was prepared by cascading a sodium metavanadate solution over a $H^+$ ion exchange resin. The sodium metavanadate concentration was 1 mole/liter.

The solution obtained was a solution of decanavanadic acid, which polymerized spontaneously.

After a few hours of aging, the solution became a dark red, viscous gel with the general formula of $V_2O_5 \cdot nH_2O$, having a $V_2O_5$ weight concentration equal to 10 to 20 g/l.

Other processes for the preparation of the $V_2O_5$ gel may be employed, such as quenching, in water, $V_2O_5$ molten at 720° C., described by P. Aldebert et al, in *J. Coll - Inter. Sci*, 98, 478 (1984), or by supercooling on a roll cooled to the temperature of liquid nitrogen, as described by L. Rivoalen et al, in *J. NON. Cr. Solids*, 21, 171 (1976).

Finally, another method, described by E. Ruiz et al, in *J. Chem. Soc. Faraday - Trans*, 1, 82, 1597-1604 (1986), also makes it possible to produce a $V_2O_5$ gel suitable for the invention. $V_2O_5$ gels may also be produced by precipitation from organic precursors.

Preparation Of Spheroidal Ionic Species Of Aluminum

A solution of the aluminum polyoxocation was prepared by the addition of a 0.2M sodium hydroxide solution to an aluminum nitrate solution having a concentration of 0.1M to 0.2M.

The $OH^-/Al$ ratio in the solution ranged from 0.5 to 2.5 and the pH ranged from 2.5 to 5.

Preferably, the solution was permitted to age, which favored the intercalation of the polyoxocation within the structure of the $V_2O_5$ gel.

The aluminum polyoxocation is described, in particular, by Johansson, in *Acta Chem. Scandinavian*, No. 3, 14 (1960).

Johansson described the structure of this cation as containing twelve octahedral aluminum atoms surrounding a tetrahedral aluminum atom. The ionic radius of this cation in the hydrated state was 12.5 Å and 5.4 Å in the nonhydrated state.

The $OH^-/Al$ ratio affects the stability of the solution and was preferably about 2.

It was also preferable to purify the solution prior to mixing it with the gel of the metallic oxide. This purification was advantageously carried out by dialysis.

Bridging of the $V_2O_5$ Gel

To the $V_2O_5$ gel thus prepared, after dilution to a concentration by weight of 0.5% in $V_2O_5$, a vanadyl sulfate solution ($VOSO_4 \cdot 5H_2O$) was added, to a concentration of $10^{-2}N$.

The mixture was vigorously agitated and the formation of a greenish precipitate was observed, due to the intercalation of vanadyl ions $VO^{++}$ with two layers of water molecules.

The product obtained, isolated and dried, had a low specific surface, on the order of 3 m²/g.

However, to insert the cation $[Al_{13}O_4(OH)_{24}]^{7+}$, the product obtained above advantageously was not separated from the reaction medium, with the prepared solution of the aluminum cation being directly added to said medium.

The resulting mixture was then maintained under agitation for about 1 hour, then permitted to age for at least 48 hours, at ambient temperature.

After aging, the product was recovered, for example by filtering or centrifuging, then washed with distilled water.

In these examples, the products were then suspended in water and dialyzed.

The products obtained in this manner were dried by heating in an oven or in a fluidized bed in air, at ambient temperature.

Characterization of the Bridged Product

The products had a porosity ranging from 0.1 cm$^3$/g to 0.4 cm$^3$/g measured by the B.E.T. method.

The porosity was stable to 250° C. and varied little up to 350+ C.

The diameters of the pores ranged from about 0.1 to 200 Å.

Analyses by RPE, infrared spectrography and X-ray diffraction evidenced that bridging had not taken place between all of the lamella of the lamellar structure.

In the following Table, the properties of the bridged vanadium oxides produced using different bridging proportions, or under different operating conditions, are reported.

As a comparison, the characteristics of an unbridged vanadium oxide are also reported.

1.6 mmole of such complex per liter of solution, was added.

After agitation, the solution was maintained for 24 hours at 60° C.

The residue obtained was centrifuged. The concentrate was then dispersed in 50 ml water.

The resulting suspension was dialyzed and then lyophilized.

The product obtained had a specific surface of approximately 15 m$^2$/g and a distance between planes of 6 Å.

Example 8

The above-described procedure was repeated, except that the solution of polynuclear molybdenum chloride was replaced by a solution of polynuclear niobium chloride containing at least 1.6 mmole of the complex per liter of solution.

The product obtained had a specific surface of approximately 18 m$^2$/g and a distance between planes of 5.2 Å.

TABLE

| Example | Solution of Aluminum polyoxocation pH | Solution of Aluminum polyoxocation R = OH$^-$/Al | Duration of aging (hours) | Ratio Al/V$_2$O$_5$ meq of Al in mixture | Weight ratio (%) Al/V in bridged V$_2$O$_5$ | Distance between planes (Å) | Specific surface m$^2$/g |
|---|---|---|---|---|---|---|---|
| 1 (V$_2$O$_5$ unbridged) | — | — | — | 0 | 0 | 0 | 2 to 3 |
| 2 | 3.92 | 1.6 | 24 | 45 | 25 | 8 | 57 |
| 3 | 4.20 | 2.3 | 24 | 45 | 29 | 8–13 | 90 |
| 4 | 4.15 | 2.5 | 24 | 45 | 30 | 8–13 | 64 |
| 5 | 4.00 | 2 | 24 | 80 | 32 | 8–13 | 90 |
| 6 | 3.95 | 2 | 48 | 120 | 32 | 8–13 | 97 |

EXAMPLES 7 AND 8

Preparation of Solutions of Spherical Ionic Species

Spherical ionic species of polynuclear molybdenum chloride 5 g MoCl$_2$ were dissolved in 1 liter dehydrated methanol. After three months, the solution was filtered to eliminate the undissolved fraction. The resulting solution was yellow. The solid Mo$_6$Cl$_{14}$ was recovered by evaporating the solvent under vacuum.

Spherical ionic species of polynuclear niobium chloride

A mixture of NbCl$_5$ and NaCl was ground and placed in a tube, together with metallic niobium. The tube was heated under vacuum at 850° C. for 6 to 8 hours and maintained at this temperature for 12 hours.

After heating, the product was extracted by successive extraction with 2 l of water containing 1 ml of concentrated HCl.

The solution was filtered and then treated with an equal volume of concentrated hydrochloric acid. The mixture was then heated and agitated until complete precipitation of Nb$_6$Cl$_{14}$·8H$_2$O was effected.

These two ionic species had the formulae of Mo$_6$Cl$_{12}{}^{2+}$ and Nb$_6$Cl$_{12}{}^{2+}$, respectively. However, the literature also indicates that these ionic species may have three positive charges.

Bridging of V$_2$O$_5$ Gel

Example 7

To the V$_2$O$_5$ gel, containing as the intercalated species vanadyl VO$^{++}$ cations, and prepared according to the procedure of Example 1, an ethanol solution of polynuclear molybdenum chloride, containing at least The invention thus enables production of a metallic oxide, such as vanadium pentoxide, having a large specific surface stable over broad ranges of temperature and having improved catalytic properties.

These compounds may be used as catalysts in numerous reactions, in particular for a variety of organic syntheses requiring a catalyst which is acid in nature.

As one such example, the catalysis of the hydroxylation of phenol with H$_2$O$_2$ will now be described:

Into a reactor, previously purged with nitrogen, 9.4 g phenol and 0.25 g of a catalyst prepared according to Example 3, were charged. The mixture was heated to 80° C. under agitation.

A solution of hydrogen peroxide, 70% by weight per volume, was injected into the mixture.

After a reaction time of 2 hours, 30 minutes, the reaction medium was filtered and the H$_2$O$_2$ content was determined by iodometry, while the diphenols pyrocatechin and hydroquinone were determined by liquid phase chromatographic analysis.

The results obtained were:

| (i) | Degree of H$_2$O$_2$ conversion | 99.5% |
|---|---|---|
| (ii) | Pyrocatechin yield relative to H$_2$O$_2$ converted | 7.5% |
| (iii) | Hydroquinone yield relative to H$_2$O$_2$ converted | 8% |
| (iv) | Total diphenol yield | 15.5% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a metallic oxide having a bridged lamellar structure, comprising (a) intimately admixing a gel of a metallic oxide having a lamellar structure with at least one member of the group consisting of (i) a solution of inorganic cations displaying an e/r ratio of greater than 1.5 wherein e is the electronic charge of the cations and r is the ionic radius thereof, in angstroms, and (ii) a solution of organic cations having a molecular diameter larger than 6 Å, (b) adding to such reaction medium a solution which comprises a spheroidal cationic species, and (c) aging the reaction medium for such period of time as to exchange the spheroidal cationic species for the cations introduced in step (a).

2. The process as defined by claim 1, further comprising recovering particulate solids of such exchanged, bridged metallic oxide.

3. The process as defined by claim 2, wherein said solids are recovered by filtration and drying.

4. The process as defined by claim 3, comprising washing said solids prior to drying.

5. The process as defined by claim 1, said metallic oxide comprising vanadium oxide, molybdenum oxide, tungsten oxide or titanium oxide.

6. The process as defined by claim 1, said spheroidal cationic species comprising a polyoxocation of aluminum, chromium, zirconium, nickel, molybdenum, niobium or tantalum.

7. The process as defined by claim 6, said spheroidal cationic species comprising $[Al_{13}O_4(OH)_{24}]^{7+}$; $[Zr_4(OH)_{12}(H_2O)_{10}]^{4+}$; $[Mo_6Cl_{14}]^{4+}$; $[Nb_6Cl_{12}]^{2+}$ or $[Ta_6Cl_{12}]^{2+}$.

8. The process as defined by claim 1, comprising intimately admixing said gel with a solution of alkaline earth, cobalt, iron, manganese, copper, strontium, lithium, vanadyl, aluminum, nickel, lanthanum or lanthanide cations.

9. The process as defined by claim 1, comprising intimately admixing said gel with a quaternary ammonium or phosphonium cation which comprises a substituted or unsubstituted alkyl radical having from 3 to 20 carbon atoms.

10. The process as defined by claim 9, said cation comprising a tetrapropyl or tetrabutyl ammonium moiety.

11. The process as defined by claim 4, said washing comprising at least one dialysis stage.

12. The process as defined by claim 2, further comprising calcining said recovered solids.

13. The process as defined by claim 5, said metallic oxide comprising vanadium pentoxide.

14. The process as defined by claim 13, said vanadium pentoxide gel comprising from 0.1% to 1% by weight of $V_2O_5$.

15. The process as defined by claim 6, said spheroidal cationic species comprising an aluminum polyoxocation.

16. The process as defined by claim 15, said gel/solution admixture comprising 13 to 50 mmole of Al per gram of $V_2O_5$.

17. A bridged, lamellar vanadium oxide, in the lattice of which the interlamellar spacing ranges from about Å to 13 Å.

18. The vanadium oxide as defined by claim 17, having a stable specific surface greater than 20 $m^2/g$.

19. The vanadium oxide as defined by claim 18, said specific surface ranging from 50 to 100 $m^2/g$.

20. The vanadium oxide as defined by claim 18, comprising from 15% to 35% by weight of aluminum.

21. The vanadium oxide as defined by claim 20, comprising from 25% to 35% by weight of aluminum.

22. In a process for the acid catalysis of an organic synthesis, the improvement which comprises utilizing as the acid catalyst therefor, the vanadium oxide catalyst as defined by claim 17.

23. The process as defined by claim 22, said organic synthesis comprising the $H_2O_2$ hydroxylation of a phenol.

* * * * *